United States Patent
Brantley et al.

(10) Patent No.: US 6,518,445 B1
(45) Date of Patent: Feb. 11, 2003

(54) METHYLALUMINOXANE COMPOSITIONS, ENRICHED SOLUTIONS OF SUCH COMPOSITIONS, AND THE PREPARATION THEREOF

(75) Inventors: Noel H. Brantley, Baton Rouge, LA (US); William R. Beard, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 214 days.

(21) Appl. No.: 09/739,052

(22) Filed: Dec. 15, 2000

(51) Int. Cl.$^7$ .................................................. C07F 5/06
(52) U.S. Cl. .................. 556/175; 556/179; 556/181; 526/160; 526/943; 502/103; 502/117
(58) Field of Search ................. 556/175, 179, 556/181; 502/103, 117; 526/160, 943

(56) References Cited

U.S. PATENT DOCUMENTS

| | | | |
|---|---|---|---|
| 3,242,099 A | 3/1966 | Manyik et al. | 252/429 |
| 4,530,914 A | 7/1985 | Ewen et al. | 502/113 |
| 4,544,762 A | 10/1985 | Kaminsky et al. | 556/179 |
| 4,701,432 A | 10/1987 | Welborn, Jr. | 502/113 |
| 4,752,597 A | 6/1988 | Turner | 502/104 |
| 4,791,180 A | 12/1988 | Turner | 526/160 |
| 4,908,463 A | 3/1990 | Bottelberghe | 556/179 |
| 4,924,018 A | 5/1990 | Bottelberghe | 556/179 |
| 4,960,878 A | 10/1990 | Crapo et al. | 556/179 |
| 5,003,095 A | 3/1991 | Beard | 556/179 |
| 5,041,583 A | 8/1991 | Sangokoya | 556/179 |
| 5,041,584 A | 8/1991 | Crapo et al. | 556/179 |
| 5,066,631 A | 11/1991 | Sangokoya et al. | 502/152 |
| 5,087,713 A * | 2/1992 | Sinn et al. | 556/179 |
| 5,099,050 A | 3/1992 | Sangokoya | 556/179 |
| 5,157,008 A | 10/1992 | Sangokoya et al. | 502/111 |
| 5,157,137 A | 10/1992 | Sangokoya | 556/179 |
| 5,235,081 A * | 8/1993 | Sangokoya | 556/179 |
| 5,248,801 A | 9/1993 | Sangokoya | 556/179 |
| 5,308,815 A | 5/1994 | Sangokoya | 502/104 |
| 5,371,260 A | 12/1994 | Sangokoya | 556/171 |
| 5,777,143 A * | 7/1998 | Malpass et al. | 556/179 |
| 5,831,109 A | 11/1998 | Smith et al. | 556/179 |
| 5,847,177 A * | 12/1998 | Sangokoya et al. | 556/179 |
| 5,917,073 A | 6/1999 | Kondoh et al. | 556/175 |
| 5,922,631 A * | 7/1999 | Sangokoya | 502/121 |
| 6,001,766 A | 12/1999 | Kissin et al. | 502/115 |
| 6,013,820 A * | 1/2000 | Sangokoya | 556/187 |

FOREIGN PATENT DOCUMENTS

JP          1258686          10/1989

OTHER PUBLICATIONS

Caplus Abstract of Article by Matthias Ott, "Optimization of Methylaluminoxane Preparation", Fortschr.–Ber. VDI, Reihe 3, (1999), 627, I–III, V–XVI, pp. 1–137.

* cited by examiner

*Primary Examiner*—Porfirio Nazario-Gonzalez
(74) *Attorney, Agent, or Firm*—Philip M. Pippenger

(57) ABSTRACT

The methylaluminoxane composition (MAOC) is a solid at 25° C. that has a total aluminum content of about 39 to 47 wt %. The MAOC is either free of aluminum as trimethylaluminum (TMA) or if TMA is present, not more than about 30 mole % of the total aluminum in the MAOC is TMA. In the solid state the MAOC contains no more than about 2000 ppm (wt/wt) of aromatic hydrocarbon. The cryoscopic number average molecular weight of MAOC as determined in benzene is at least about 1000 amu, and the MAO has sufficient solubility in n-heptane at 25° C. to provide a solution containing 4 to as high as 7.5 wt % or more of dissolved aluminum. By vacuum distilling a solution of ordinary MAO in aromatic hydrocarbon long enough under proper conditions, MOAC is formed.

59 Claims, No Drawings

METHYLALUMINOXANE COMPOSITIONS, ENRICHED SOLUTIONS OF SUCH COMPOSITIONS, AND THE PREPARATION THEREOF

TECHNICAL FIELD

This invention relates to the provision of novel methylaluminoxane compositions, to especially useful solutions of such methylaluminoxanes in hydrocarbon solvents other than aromatic hydrocarbon solvents, and to the preparation of such compositions and solutions.

In the ensuing description and in the claims hereof, reference is sometimes made to solubility in n-heptane because this is a typical, representative saturated hydrocarbon which serves as a very convenient point of reference for comparisons of solubility. However, such references to n-heptane does not constitute a limitation or restriction on the scope of this invention as regards hydrocarbons used, as the invention produces methylaluminoxane compositions that have improved solubility in a variety of liquid aliphatic and cycloaliphatic hydrocarbons as compared to the solubility of previously reported methylaluminoxane in the same respective hydrocarbons.

BACKGROUND

Hydrocarbylaluminoxanes complexed with transition metal compounds are known to be effective olefin polymerization catalysts. See for example, U.S. Pat. No. 3,242,099 to Manyik et al. Methylaluminoxanes prepared by partial hydrolysis of trimethylaluminum under various conditions are commonly-used effective co-catalyst components. However as is well known, methylaluininoxanes have been found to have poor solubility in non-aromatic hydrocarbon solvents. See in this regard, U.S. Pat. Nos. 4,960,878 to Crapo et al.; 5,041,584 to Crapo et al.; 5,066,631 to Sangokoya et al.; 5,308,815 to Sangokoya; 5,847,177 to Sangokoya et al.; 6,001,766 to Kissin et al., and Japan Kokai 01/258,686 to Kioka et al.

Disclosures from which it is possible to calculate or at least estimate total aluminum concentrations in non-aromatic solvents include U.S. Pat Nos. 4,530,914 to Ewen et al.;

U.S. Pat. No. 4,544,762 to Kaminsky et al.; U.S. Pat. No. 4,701,432 to Welborn; U.S. Pat. No. 4,752,597 to Turner; U.S. Pat. No. 4,791,180 to Turner; and U.S. Pat. No. 5,066,631 to Sangokoya et al.; and Ott, University of Hamburg Thesis, 1999. It appears that the highest reported total aluminum concentration in these documents is 3.85 wt % in heptane—see Example 3 of U.S. Pat. No. 5,066,631 to Sangokoya et al. It appears from an abstract of a paper by Matthias Ott, entitled *Optimization of Methylaluminoxane Preparation*, Fortschr.-Ber. VDI Reihe 3 (1999),627, I–III, V–XVI, 1–137 (Accession number 2000:106460 CAPLUS) that it is speculated that it will be possible to prepare methylaluminoxane solutions of up to 10% in heptane with the use of the "Eisbandreaktor" referred to therein.

The poor solubility of methylaluminoxanes in non-aromatic solvents is most unfortunate because polyolefin manufacturers of products that come into contact with foodstuffs desire to minimize as much as possible, if not eliminate, aromatic hydrocarbons from the raw materials and processing operations used. The manufacturers would much prefer raw materials and operations in which less toxic non-aromatic hydrocarbons are employed.

Considerable past efforts have been devoted to various ways of modifying methylaluminoxanes in order to increase their solubility in non-aromatic hydrocarbons. These efforts generally involve either the addition or inclusion of other components to improve such solubility, or the treatment of the methylaluminoxane in such a way that a substantial portion of methylaluminoxane, e.g., at least 25 percent by weight of the total methylaluminoxane on a dry basis, exists or remains as a precipitate and is not included in the solution. Such precipitates are believed -to be composed of higher molecular weight oligomers and are isolated by filtration, decantation, or other liquid-solids physical separation procedure.

Whatever their makeup, such precipitates are usually discarded as waste, thereby leaving in solution a lower molecular weight methylaluminoxane fraction which generally contains more than about 30 mole percent trimethylaluminum and is more soluble in non-aromatic solvents. A number of examples of such approaches are described in the patent literature.

It would be of considerable advantage if a way could be found of providing new methylaluminoxane compositions having superior solubility characteristics in various non-aromatic hydrocarbons, especially paraffinic and cycloparaffinic hydrocarbons, without need for (a) addition or inclusion of other components to improve such solubility, or (b) treatment of the methylaluminoxane in such manner that results in loss of a substantial portion of its original content.

THE INVENTION

This invention involves, inter alia, the discovery that it is indeed possible to form and provide such new methylaluminoxane compositions having significantly higher solubility in non-aromatic hydrocarbons without addition of any third component to increase solubility, and without recourse to processing that removes substantial portions of higher molecular weight components from the methylaluminoxane.

Accordingly, in one of its embodiments this invention provides a methylaluminoxane composition wherein:

A) the composition is a solid at 25° C.;

B) the composition has a total aluminum content in the range of about 39 to about 47 wt % based on the total weight of the composition in the solid state;

C) the composition is either free of aluminum in the form of trimethylaluminum or if trimethylaluminum is present in the composition, not more than about 30 mole %, preferably no more than about 20 mole %, and most preferably no more than about 10 mole % of the total aluminum present in the composition is in the form of trimethylaluminum;

D) the composition in the solid state contains no more than about 2000 ppm (wt/wt) of aromatic hydrocarbon;

E) the cryoscopic number average molecular weight of the composition as determined in benzene is at least-about 1000, preferably at least about 1100, and more preferably at least about 1200 atomic mass units; and F) the composition has sufficient solubility in n-heptane at 25° C. to provide a solution containing at least 4 wt %, preferably at least 5 wt %, and most preferably at least 7.5 wt % of dissolved aluminum.

Another embodiment of this invention is a method of preparing the above 5 methylaluminoxane compositions. The method comprises subjecting a solution of methylaluminoxane in an aromatic hydrocarbon solvent to distillation at a temperature no higher than about 25° C. under reduced pressure of below $1 \times 10^{-5}$ millimeters of mercury to form a solid methylaluminoxane composition that complies with each of the criteria set forth above as A) through F), inclusive.

Pursuant to another embodiment of this invention there is provided a composition which comprises a solution of methylaluminoxane in a non-aromatic hydrocarbon solvent, wherein:

a) if any trimethylaluminum is present in the solution, no more than about 30 mole %, preferably no more than about 20 mole %, and more preferably no more than about 10 mole % of the total dissolved aluminum in the solution is trimethylaluminum;

b) the solution has a total dissolved aluminum content above 4 wt %, preferably 5 wt % or more, and more preferably at least about 7.5 wt %, based on the total weight of all dissolved aluminum components of the methylaluminoxane plus the weight of the non-aromatic hydrocarbon solvent;

c) the solution contains, if any, no more than 2000 ppm (wt/wt) of aromatic hydrocarbon, based on the total weight of all dissolved aluminum components of the methylaluminoxane plus the total weight of the hydrocarbon solvent (i.e., including the weight of the aromatic hydrocarbon, if any, in the solution); and d) the methylaluminoxane in the solution has a cryoscopic number average molecular weight as determined in benzene of at least 1000, more preferably at least 1100, and most preferably at least 1200 atomic mass units.

Still another embodiment of this invention is a method of preparing the compositions of the immediately preceding paragraph. The method comprises subjecting a solution of methylaluminoxane in an aromatic hydrocarbon solvent to distillation at a temperature no higher than about 25° C. under reduced pressure of about $1 \times 10^{-5}$ millimeters of mercury or less to form a solid methylaluminoxane residue that has (i) an aluminum content in the range of about 39 to about 47 wt %, (ii) a trimethylaluminum content, if any, of no more than about 30 mole %, preferably no more than about 20 mole %, and more preferably no more than about 10 mole % of the total aluminum content of the residue, and (iii) a cryoscopic number average molecular weight as determined in benzene of at least 1000, more preferably at least 1100, and most preferably at least 1200 atomic mass units; and dissolving such solid methylaluminoxane residue in a non-aromatic hydrocarbon solvent in an amount such that the resultant solution contains at least 4 wt %, preferably at least about 5 wt %, and more preferably at least about 7.5 wt % of dissolved aluminum based on the weight of these specified components.

The method to be used in determining the mole percentage of trimethylaluminum in the methylaluminoxane, in any case where it is desired or deemed necessary to determine such mole percentage, is identified hereinafter and is referred to in this document as the NMR Analytical Procedure. It is described in "Characterization of Methylaluminoxanes and Determination of Trimethylaluminum Using Proton NMR" by Donald W. Imhoff, Larry S. Simeral, Samuel A. Sangakoya, and James H. Peel; *Organometallics*, 1998, 17, 1941–1945.

These and other embodiments and features of this invention will become further apparent from the ensuing description and appended claims.

FURTHER DETAILED DESCRIPTION

New Methylaluminoxane Compositions and their Preparation

The methylaluminoxanes (a.k.a. methylalumoxanes) components utilized as starting materials in forming the aromatic hydrocarbon solution prior to distillation are essentially the same as those made commercially in aromatic solvents (e.g. toluene). They are characterized by evolving, when subjected to hydrolysis with water, methane, as well as very small amounts of hydrogen and hydrocarbon molecules which are larger than methane, such as, for example, ethane, propane, isobutane and n-butane. These alkanes larger than methane result from impurities in the trimethylaluminum from which the methylaluminoxane is produced. No organoaluminum compound other than trimethylaluminum of typical commercial purity (e.g., 98% or more) should be used in forming or be added to the methylaluminoxane starting material.

Either of two different types of processes are usually, but not necessarily, used for producing the methylaluminoxanes used as starting materials in the practice of this invention. One such well-known process involves controlled, partial hydrolysis of trimethylaluminum with free water or with water derived from a hydrated metal salt. Processes of this type are described, for example, in U.S. Pat. Nos. 4,908,463; 4,924,018; 5,003,095; 5,041,583; 5,066,631; 5,099,050; 5,157,008; 5,157,137; 5,235,081; 5,248,801, and 5,371,260. Methyl-aluminoxanes typically contain varying amounts, of from about 5 to 35 mole percent, of the aluminum value as unreacted trimethylaluminum. Preferably, the aluminum content as trimethylaluminum is less than about 23 mole percent of the total aluminum value, and, more ipreferably, less than about 20 mole percent. The other process involves treating trimethylaluminum with a compound containing an oxygen-carbon bond such as carbon dioxide, benzoic acid, benzophenone, acetone and the like. See in this connection, U.S. Pat. No. 5,831,109, entitled "Polyaluminoxane Compositions Formed by Non-Hydrolytic Means".

Often the methylaluminoxane as produced and offered for sale in the marketplace is in the form of a solution in an aromatic hydrocarbon, typically toluene. Such solutions usually contain 10 or 30 wt % of the methylaluminoxane, and it is convenient (but of course not necessary) to use such solutions in preparing the new methylaluminoxane compositions of this invention.

A solution of the conventional methylaluminoxane in an aromatic hydrocarbon solvent is subjected to distillation under reduced pressure conditions at a temperature no higher than about 30° C. for a period of time long enough not only to remove the liquid phase but to produce a solid product satisfying the above criteria of A) through F) inclusive. Preferably the distillation is performed at ambient room temperature, e.g., at temperatures in the vicinity of 25° C. The pressure during distillation is maintained below about $1 \times 10^{-5}$ millimeters of mercury, with a pressure of less than about $5 \times 10^{-6}$ millimeters of mercury being more desirable. The time period for the vacuum distillation will of course vary depending upon such factors as the concentration of the initial solution of the methylaluminoxane, the aromatic hydrocarbon used as the solvent for such solution, and the reduced pressure employed. Times in the range of about 4 to about 120 hours may suffice, but in any case where suitable or optimal time-temperature-pressure conditions for any given initial aromatic hydrocarbon solution of methylaluminoxane have not been previously ascertained, a few pilot experiments on a laboratory scale coupled with product analyses and evaluations will enable determination of conditions to be used. Examples 1 and 2 hereinafter provide conditions known to be very satisfactory with the methylaluminoxane solutions used therein.

It will of course be understood that the process of preparing a methylaluminoxane of this invention should be conducted under suitably inert and anhydrous conditions.

The solid methylaluminoxane composition of this invention is the residue formed upon distillation, and thus it has an aluminum content in the range of from about 39 to about 47 wt %, and more preferably in the range of from about 41 to about 45 wt %. Most preferable is an aluminum content in the range of from about 42 to about 44 wt %. Usually the solid methylaluminoxane composition will contain some trimethylaluminum, and when it does, not more than 30 mole %, preferably no more than 20 mole %, and more preferably no more than 10 mole % of the aluminum in the composition is in the form of trimethylaluminum, all as determined by the aforementioned NMR Analytical Procedure. The content, if any, of aromatic hydrocarbon in the compositions of this invention may also conveniently be determined by proton NMR spectroscopy using the aforementioned published NMR Analytical Procedure. In the event of disparate results from different methods of determining the aromatic hydrocarbon content of such compositions, the value as determined by such published NMR procedure should control. The cryoscopic molecular weight of the composition is determined by using benzene, rather than 1,4-dioxane, as the cryoscopic solvent in the procedure described in "Determination of Trimethylaluminum and Characterization of Methylaluminoxanes Using Proton NMR" by Donald W. Imhoff, Larry S. Simeral, Don R. Blevins, and William R. Beard; ppg 177–191 of ACS Symposium Series 749, Olefin Polymerization: Emerging Frontiers; Palanisamy Arjunan, James E. McGrath, and Thomas L. Hanlon, Eds.; copyright 2000 by the American Chemical society, Washington, D.C.

SOLUTIONS OF THIS INVENTION AND THEIR FORMATION

To form the solutions of this invention one either (i) prepares a solid methylaluminoxane of this invention and dissolves all or a portion of such composition in a suitable non-aromatic hydrocarbon solvent, or (ii) if a solid composition of this invention has already been prepared and provided for use, all or a portion of such composition is used in preparing a solution of this invention, or (iii) the methylaluminoxane solution may be prepared directly in the non-aromatic solvent, that is, by reacting trimethylaluminum with a suitable reagent (e.g., water or benzoic acid) in the non-aromatic solvent. Alternative (i) typically involves preparing the solid methylaluminoxane composition (reduced pressure distillation residue) at the site where the solution will be formed. Alternative (ii) typically involves preparing a solid composition of this invention at a plant site which is not necessarily the site at which the solution of this invention will be prepared. In this second case one preparing the solution will typically purchase the solid methylaluminoxane of this invention from the manufacturer thereof. Thus the overall process of this invention (making and dissolving) can be conducted by one party typically at one plant site or by two or more different parties typically at different plant sites (making at one plant site, and dissolving at another plant site). All such alternatives are within the scope of this invention.

Any saturated or unsaturated non-aromatic hydrocarbon, mixture of two or more saturated hydrocarbons, mixture of two or unsaturated non-aromatic hydrocarbons, or mixture of one or more saturated and one or more unsaturated non-aromatic hydrocarbons that exist as a liquid at least throughout the range of about 20 to about 30° C. can be used as the solvent in the hydrocarbon solutions of this invention. Preferred hydrocarbon solvents of this type used in the practice of this invention include (a) one or more alkane, alkene, alkadiene, cycloalkane, cycloalkene, cycloalkadiene, or alkyne hydrocarbons, that exist as a liquid at least throughout the range of about 20 to about 30° C.; or (b) a mixture of at least two of (a); or (c) at least one of (a) and/or (b), and one or more alkane hydrocarbons that exist as a liquid at least throughout the range of about 20 to about 30° C. A few non-limiting examples of such hydrocarbons include n-pentane, isopentane, cyclopentane, 1-pentene, 2-pentene, n-hexane, 2-methylpentane, 3-methylpentane, cyclohexane, 1-hexene, 2-hexene, 3-hexene, cyclohexene, 1,5-hexadiene. methylcyclohexane, n-heptane, 2-methylheptane, 3-methylheptane, 4-methylheptane, 1-heptyne, 2-heptyne, 3-heptyne, n-octane, 1-octene, octadiene, 2,2,4-trimethylpentane, 1,3,5,7-cyclooctatetraene, n-nonane, n-decane, 1-decene, 1-decyne, 5-decyne, α-pinene, decahydronaphthalene, n-dodecane, and pentadecane.

In forming the solutions of this invention, it is desirable that if trimethylaluminum is present in the solid methylaluminoxane composition of this invention being used to form the solution, no more than about 30 mole % of the total dissolved aluminum be present as trimethylaluminum. It is more desirable that no more than 20 mole %, and still more desirable that no more than 10 mole % of the total dissolved aluminum be present as trimethylaluminum, as determined by the aforementioned NMR Analytical Procedure.

Typically, the methylaluminoxane solution has a total dissolved aluminum content above about 4 wt % and more preferably above about 5 wt %. Most preferable is a total dissolved aluminum content which is above about 7.5 wt %. The total dissolved aluminum content is based on the total weight of all dissolved aluminum species which are components of the methylaluminoxane plus the weight of the nonaromatic hydrocarbon solvent. Thus when forming the methylaluminoxane solution the solid methylaluminoxane of this invention is dissolved in a non-aromatic hydrocarbon solvent in amounts such that the methylaluminoxane solution produced contains an amount of dissolved aluminum in accordance with the foregoing. Of course if one wishes to do so, the amount of the solid methylaluminoxane of this invention dissolved in a non-aromatic hydrocarbon solvent can be less than about 4 wt %.

The methylaluminoxane solutions of this invention contain, if any, no more than about 2000 ppm (wt/wt) of aromatic hydrocarbon. Preferably, the solutions contain no more than about 500 ppm, and most preferably no more than about 100 ppm, of aromatic hydrocarbon. The indicated ppm determinations are based upon the total weight of all dissolved aluminum species which are components of the solid methylaluminoxane composition plus the total weight of the hydrocarbon solvent, including aromatic solvent components, if any.

The cryoscopic number average molecular weight, as determined in benzene solution, of the methylaluminoxane in solution is at least about 1000 atomic mass units (amu), preferably above about 1100 amu, and most preferably above about 1200 amu.

When forming the methylaluminoxane solution by the process of the invention, the solid methylaluminoxane composition (e.g., reduced pressure distillation residue) is dissolved in a non-aromatic hydrocarbon solvent in amounts such that the methylaluminoxane solution produced will typically contain at least about 4 wt %, preferably at least 5 wt %, of dissolved aluminum, and more preferably at least about 7.5 wt %. Weight percent of dissolved aluminum is based upon the weight of the solid methylaluminoxane composition (e.g., reduced pressure distillation residue) dissolved in the non-aromatic hydrocarbon solvent, as well as weight of the non-aromatic hydrocarbon solvent.

When the methylaluminoxane compositions and solutions of this invention are hydrolyzed, whether in solid form or in solution, the non-methane hydrocarbon hydrolysis products are the same as those formed from hydrolysis of commercial grades of trimethylaluminum and commercial grades of aromatic-solvent solutions of methylaluminoxanes in that the non-methane hydrocarbon hydrolysis products contain, if any, no more than about 2 mole percent of other hydrocarbons formed during the hydrolysis reaction. Furthermore, they contain essentially no detectable amount of any other hydrocarbon except perhaps at most 2000 ppm (wt/wt) of trace residual amounts of aromatic hydrocarbon (usually toluene) in which the methylaluminoxane had been dissolved before being isolated from such solution. Thus the methylaluminoxane solutions of the present invention are "all-methyl aluminoxanes" in that they have been produced from trimethylaluminum of standard commercial purity, and no other organoaluminum compound has been added either to the trimethylaluminum used in forming the methylaluminoxane, or to the methylaluminoxane itself. The traces of vaporous hydrocarbon(s) typically, but not necessarily, released on aqueous hydrolysis of the methylaluminoxane probably result from trace amounts of impurities present in the original trimethylaluminum used as the starting material for producing the methylaluminoxane.

The following Examples are presented for purposes of illustration and are not intended to limit, do not limit, and should not be construed as limiting, the generic scope of this invention.

Examples 1 and 2 illustrate methods of producing solid methylaluminoxanes pursuant to this invention.

EXAMPLE 1

A 30 wt % methylaluminoxane (MAO) in toluene solution, which was produced in a commercial plant by the direct hydrolysis of trimethylaluminum with free water, was vacuum stripped to dryness at ambient temperatures in the range of 18 to 27° C. at pressures as low as about $1\times10^{-6}$ millimeters of mercury for sixteen days. A friable, white solid MAO product was obtained which, when subjected to the above NMR Analytical Procedure, was found to contain 8.59 mole % of trimethylaluminum, and 0.52 wt % of toluene. The aluminum content of the product, determined by acid digestion followed by EDTA titration, was 42.81 wt %; and its number average molecular weight, determined by cryoscopy in benzene solvent, was 1593 atomic mass units (amu).

EXAMPLE 2

In a nitrogen atmosphere, 740 grams of toluene and 113.2 grams of trimethylaluminum were heated to 50° C. To this solution was added 77.0 grams of ferrous sulfate heptahydrate in four equal increments over a two-hour period. The solution was kept at 50° C. for an additional 6 hours. Solids were removed by centrifugation, leaving a clear supernatant liquid containing 3.42 wt % aluminum. NMR analysis indicated the formation of a methylaluminoxane. A portion of the supernatant solution was vacuum stripped to dryness for approximately 6 hours at $1\times10^{-5}$ (i.e., 0.00001) millimeters of mercury and at ambient temperatures in the range of about 18 to 27° C.

The friable, white solid MAO product, when subjected to the above NMR Analytical Procedure, was found to contain 12 mole % of trimethylaluminum and 0.3 wt % toluene. The aluminum content of the product, determined by acid digestion followed by EDTA titration, was 42.3 wt %; and its number average molecular weight, determined by cryoscopy in benzene solvent, was 1166 amu.

Examples 3–20 illustrate the solubility of MAO in various hydrocarbon solvents formed from 30 wt % slurries of MAO.

EXAMPLES 3–20

In a nitrogen atmosphere at ambient temperatures, individually weighed portions of solid MAO from either Example 1 or Example 2 were combined with various aliphatic hydrocarbons in proportions such that slurries containing 30 wt % MAO were formed. After thorough mixing, the solid MAO which did not dissolve was collected by centrifugation and dried. The amount of MAO that dissolved was obtained by taking the difference between the amount of MAO initially added and the amount of solvent-free solid MAO that had centrifuged out of the solution. The amount of MAO centrifuged out of solution was determined by vacuum removal of any traces of solvent and weighing of the resultant solvent-free solid. Table I sets forth the weight percentage of the solid MAO that dissolved in each respective solvent and the weight percentage of aluminum present in each of the respective solutions.

TABLE I

| Example | Solvent | Amount (wt %) of Solid MAO Dissolved | Calculated wt % MAO in Solution | Calculated wt % Aluminum in Solution[1] | Calculated Mole % TMA in Solution[2] | Calculated wt % Toluene in Solution[3] | Wt % Aluminum in Solution Found by Analysis | Source of MAO | Wt % Al in MAO | Mole % TMA in MAO | Wt % Toluene in MAO |
|---|---|---|---|---|---|---|---|---|---|---|---|
| 3 | cyclohexane | 91% | 28.1% | 12.0% | 9.44% | 0.16% | — | Ex 1 | 39.6% | 8.59% | 0.52% |
| 4 | methylcyclohexane | 94% | 28.7% | 12.3% | 9.14% | 0.16% | 12.8% | Ex 1 | 39.6% | 8.59% | 0.52% |
| 5 | methylcyclohexane | 93% | 28.5% | 12.1% | 12.90% | 0.09% | — | Ex 2 | 42.3% | 12.0% | 0.30% |
| 6 | pentane | 67% | 22.3% | 9.6% | 12.82% | 0.17% | — | Ex 1 | 39.6% | 8.59% | 0.52% |
| 7 | hexane | 67% | 22.3% | 9.6% | 12.82% | 0.17% | — | Ex 1 | 39.6% | 8.59% | 0.52% |
| 8 | hexane | 78% | 25.1% | 10.6% | 15.38% | 0.10% | — | Ex 2 | 42.3% | 12.0% | 0.30% |
| 9 | heptane | 63% | 21.3% | 9.1% | 13.63% | 0.18% | — | Ex 1 | 39.6% | 8.59% | 0.52% |
| 10 | heptane | 72% | 23.6% | 10.0% | 16.67% | 0.10% | — | Ex 2 | 42.3% | 12.0% | 0.30% |
| 11 | octane | 58% | 19.9% | 8.5% | 14.81% | 0.18% | — | Ex 1 | 39.6% | 8.59% | 0.52% |
| 12 | iso-pentane | 72% | 23.6% | 10.1% | 11.93% | 0.17% | — | Ex 1 | 39.6% | 8.59% | 0.52% |
| 13 | 3-methylpentane | 75% | 24.3% | 10.4% | 11.45% | 0.17% | — | Ex 1 | 39.6% | 8.59% | 0.52% |
| 14 | cyclopentane | 96% | 29.1% | 12.5% | 8.95% | 0.16% | 13.4% | Ex 1 | 39.6% | 8.59% | 0.52% |
| 15 | cyclopentane | 97% | 29.4% | 12.4% | 12.37% | 0.09% | — | Ex 2 | 42.3% | 12.0% | 0.30% |

TABLE I-continued

| Example | Solvent | Amount (wt %) of Solid MAO Dissolved | Calculated wt % MAO in Solution | Calculated wt % Aluminum in Solution[1] | Calculated Mole % TMA in Solution[2] | Calculated wt % Toluene in Solution[3] | Wt % Aluminum in Solution Found by Analysis | Source of MAO | Wt % Al in MAO | Mole % TMA in MAO | Wt % Toluene in MAO |
|---|---|---|---|---|---|---|---|---|---|---|---|
| 16 | Isopar E | 61% | 20.7% | 8.9% | 14.08% | 0.18% | — | Ex 1 | 39.6% | 8.59% | 0.52% |
| 17 | Isopar G | 37% | 13.7% | 5.9% | 23.22% | 0.19% | — | Ex 1 | 39.6% | 8.59% | 0.52% |
| 18 | cycloheptane | 57% | 19.6% | 8.4% | 15.07% | 0.18% | — | Ex 1 | 39.6% | 8.59% | 0.52% |
| 19 | cyclooctane | 30% | 11.4% | 4.9% | 28.63% | 0.20% | — | Ex 1 | 39.6% | 8.59% | 0.52% |
| 20 | isohexane | 69% | 22.8% | 9.8% | 12.45% | 0.17% | — | Ex 1 | 39.6% | 8.59% | 0.52% |

[1]Assumes equal aluminum contents for the soluble and insoluble portions.
[2]Assumes all TMA present in the solid MAO was extracted into the solution. This assumption slightly over-estimates the TMA contents of the solution.
[3]Assumes all toluene present in the solid was extracted into the solution.

EXAMPLES 21–45

In a nitrogen atmosphere at ambient temperatures, individual weighed portions of solid MAO from Example 1 were combined with various olefinic hydrocarbons in proportions such that slurries containing 30 wt % MAO were formed. After thorough mixing, the solid MAO which did not dissolve was collected by centrifugation. The amount of MAO that dissolved was determined as described for Examples 3–20. Table II sets forth the weight percentage of the solid MAO that dissolved in each respective solvent and the weight percentage of aluminum present in each of the respective solutions.

EXAMPLES 46–61

In a nitrogen atmosphere at ambient temperatures, individual weighed portions of solid MAO from Example 1 were combined with various mixtures of hydrocarbons in proportions such that slurries containing 30 wt % MAO were formed. After thorough mixing, the solid MAO which did not dissolve was collected by centrifugation. The amount of MAO that dissolved was determined as described for Examples 3–20. Table III sets forth the weight percentage of the solid MAO that dissolved in each respective solvent mixture, the weight percentage of aluminum present in each of the respective solutions, and the relative amounts (wt %) of each solvent in the solvent mixture.

TABLE II

| Example | Solvent | Amount (wt %) of Solid MAO Dissolved | Calculated wt % MAO in Solution | Calculated wt % Aluminum in Solution[4] | Calculated Mole % TMA in Solution[5] | Calculated wt % Toluene in Solution[6] |
|---|---|---|---|---|---|---|
| 21 | 1-pentene | 85% | 26.7% | 11.4% | 10.11% | 0.16% |
| 22 | 1-hexene | 97% | 29.4% | 12.6% | 8.86% | 0.16% |
| 23 | 1-octene | 89% | 27.6% | 11.8% | 9.65% | 0.16% |
| 24 | 1-decene | 66% | 22.0% | 9.4% | 13.02% | 0.17% |
| 25 | 2-pentene | 72% | 23.6% | 10.1% | 11.93% | 0.17% |
| 26 | 1,4-cyclooctadiene | 94% | 28.7% | 12.3% | 9.14% | 0.16% |
| 27 | 1,5-hexadiene | 91% | 28.1% | 12.0% | 9.44% | 0.16% |
| 28 | 4-vinyl-1-cyclohexene | 91% | 28.1% | 12.0% | 9.44% | 0.16% |
| 29 | cyclohexene | 94% | 28.7% | 12.3% | 9.14% | 0.16% |
| 30 | 1,3-cyclohexadiene | 96% | 29.1% | 12.5% | 8.95% | 0.16% |
| 31 | 1-methyl-1,3-cyclohexadiene | 80% | 25.5% | 10.9% | 10.74% | 0.17% |
| 32 | cyclooctene | 89% | 27.6% | 11.8% | 9.65% | 0.16% |
| 33 | 1,3-cyclooctadiene | 95% | 28.9% | 12.4% | 9.04% | 0.16% |
| 34 | 1-tert-butyl-1-cyclohexene | 6% | 2.5% | 1.1% | >100% | 0.22% |
| 35 | 1-isopropyl-1-cyclohexene | 33% | 12.4% | 5.3% | 26.03% | 0.20% |
| 36 | 4-methyl-1-cyclohexene | 94% | 28.7% | 12.3% | 9.14% | 0.16% |
| 37 | 2,5-dimethyl-2,4-hexadiene | 94% | 28.7% | 12.3% | 9.14% | 0.16% |
| 38 | limonene | 91% | 28.1% | 12.0% | 9.44% | 0.16% |
| 39 | 4-methyl-1-hexene | 86% | 26.9% | 11.5% | 9.99% | 0.16% |
| 40 | 2,3-dimethyl-2-hexene | 34% | 12.7% | 5.4% | 25.26% | 0.19% |
| 41 | 2,5-dimethyl-1,5-hexadiene | 96% | 29.1% | 12.5% | 8.95% | 0.16% |
| 42 | 7-methyl-1,4-cyclooctadiene | 94% | 28.7% | 12.3% | 9.14% | 0.16% |
| 43 | 2-methyl-1,5-hexadiene | 96% | 29.1% | 12.5% | 8.95% | 0.16% |
| 44 | trans-3-hexene | 57% | 19.6% | 8.4% | 15.07% | 0.18% |
| 45 | 2-methyl-1-hexene | 90% | 27.8% | 11.9% | 9.54% | 0.16% |

[4]Assumes equal aluminum contents for the soluble and insoluble portions.
[5]Assumes all TMA present in the solid MAO was extracted into the solution. This assumption slightly over-estimates the TMA contents of the solution.
[6]Assumes all toluene present in the solid was extracted into the solution.
[7]The calculated amount of TMA in the solution was greater than 100%.

TABLE III

| Example | Solvent 1 | Amount of Solvent 1 in Solvent Mixture | Solvent 2 | Amount of Solvent 2 in Solvent Mixture | Amount (wt %) of Solid MAO Dissolved | Calculated wt % MAO in Solution | Calculated wt % Aluminum in Solution[8] | Calculated Mole % TMA in Solution[9] | Calculated wt % Toluene in Solution[10] |
|---|---|---|---|---|---|---|---|---|---|
| 46 | cyclopentane | 74% | heptane | 26% | 90% | 27.8% | 11.9% | 9.54% | 0.16% |
| 47 | cyclopentane | 50% | heptane | 50% | 76% | 24.6% | 10.5% | 11.30% | 0.17% |
| 48 | cyclopentane | 25% | heptane | 75% | 61% | 20.7% | 8.9% | 14.08% | 0.18% |
| 49 | cyclopentane | 51% | methylcyclohexane | 49% | 90% | 27.8% | 11.9% | 9.54% | 0.16% |
| 50 | cyclopentane | 50% | 1-octene | 50% | 89% | 27.6% | 11.8% | 9.65% | 0.16% |
| 51 | cyclopentane | 98% | 1,4-cyclooctadiene | 2% | 90% | 27.8% | 11.9% | 9.54% | 0.16% |
| 52 | methylcyclohexane | 75% | heptane | 25% | 78% | 25.1% | 10.7% | 11.01% | 0.17% |
| 53 | methylcyclohexane | 51% | heptane | 49% | 68% | 22.6% | 9.7% | 12.63% | 0.17% |
| 54 | methylcyclohexane | 26% | heptane | 74% | 58% | 19.9% | 8.5% | 14.81% | 0.18% |
| 55 | methylcyclohexane | 50% | 1-octene | 50% | 85% | 26.7% | 11.4% | 10.11% | 0.16% |
| 56 | methylcyclohexane | 98% | 1,4-cyclooctadiene | 2% | 89% | 27.6% | 11.8% | 9.65% | 0.16% |
| 57 | heptane | 50% | 1-octene | 50% | 64% | 21.5% | 9.2% | 13.42% | 0.17% |
| 58 | heptane | 96% | 1,4-cyclooctadiene | 4% | 54% | 18.8% | 8.0% | 15.91% | 0.18% |
| 59 | heptane | 98% | 1,4-cyclooctadiene | 2% | 51% | 17.9% | 7.7% | 16.84% | 0.18% |
| 60 | heptane | 99% | 1,4-cyclooctadiene | 1% | 52% | 18.2% | 7.8% | 16.52% | 0.18% |
| 61 | 1-octene | 98% | 1,4-cyclooctadiene | 2% | 74% | 24.1% | 10.3% | 11.61% | 0.17% |

[8]Assumes equal aluminum contents for the soluble and insoluble portions.
[9]Assumes all TMA present in the solid MAO was extracted into the solution. This assumption slightly over-estimates the TMA contents of the solution.
[10]Assumes all toluene present in the solid was extracted into the solution.

EXAMPLES 62–73

Examples 62–70 illustrate the solubility of MAO in various hydrocarbon solvents when the MAO solutions were formed from slurries having differing MAO content.

In a nitrogen atmosphere at ambient temperatures, individual weighed portions of solid MAO from Example 1 were combined with various saturated hydrocarbons, in proportions such that slurries containing 5, 15 and 45 wt % MAO were formed. After thorough mixing, the solid MAO which did not dissolve was collected by centrifugation. The amount of MAO that dissolved was determined as described for Examples 3–20. Table IV sets forth the amounts of solid MAO that dissolved in each respective solvent mixture along with the mole % trimethylaluminum, wt % aluminum, and wt % toluene present in each of the respective solutions.

TABLE IV

| Example | Solvent | Slurry wt % MAO | Amount (wt %) of Solid MAO Dissolved | Calculated wt % MAO in Solution | Calculated wt % Aluminum in Solution[11] | Calculated Mole % TMA in Solution[12] | Calculated wt % Toluene in Solution[13] |
|---|---|---|---|---|---|---|---|
| 62 | cyclopentane | 5 | 92% | 4.6% | 2.0% | 9.34% | 0.16% |
| 63 | cyclopentane | 15 | 92% | 14.0% | 6.0% | 9.34% | 0.16% |
| 64 | cyclopentane | 45 | 94% | 43.5% | 18.6% | 9.14% | 0.16% |
| 65 | methylcyclohexane | 5 | 82% | 4.1% | 1.8% | 10.48% | 0.16% |
| 66 | methylcyclohexane | 15 | 83% | 12.8% | 5.5% | 10.35% | 0.16% |
| 67 | methylcyclohexane | 45 | 90% | 42.4% | 18.2% | 9.54% | 0.16% |
| 68 | heptane | 5 | 73% | 3.7% | 1.6% | 11.77% | 0.17% |
| 69 | heptane | 16 | 57% | 9.8% | 4.2% | 15.07% | 0.18% |
| 70 | heptane | 46 | 56% | 32.3% | 13.8% | 15.34% | 0.18% |

[11]Assumes equal aluminum contents for the soluble and insoluble portions.
[12]Assumes all TMA present in the solid MAO was extracted into the solution. This assumption slightly over-estimates the TMA contents of the solution.
[13]Assumes all toluene present in the solid was extracted into the solution.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A methylaluminoxane composition wherein (A) the composition is a solid at 25° C.; (B) the composition has a total aluminum content in the range of about 39 to about 47 wt % based on the total weight of the composition in the solid state; (C) the composition is either free of aluminum in the form of trimethylaluminum or if trimethylaluminum is present in the composition, not more than about 30 mole % of the total aluminum present in the composition is in the form of trimethylaluminum; (D) the composition in the solid state contains no more than about 2000 ppm (wt/wt) of aromatic hydrocarbon; (E) the cryoscopic number average molecular weight of the composition as determined in benzene is at least about 1000 atomic mass units; and (F) the composition has sufficient solubility in n-heptane at 25° C. to provide a solution containing at least 4 wt % of dissolved aluminum.

2. A composition of claim 1 wherein if trimethylaluminum is present in the composition, no more than about 20 mole % of the total aluminum present in the composition is in the form of trimethylaluminum.

3. A composition of claim 1 wherein if trimethylaluminum is present in the composition, no more than about 10 mole % of the total aluminum present in the composition is in the form of trimethylaluminum.

4. A composition of claim 1 wherein said cryoscopic number average molecular weight of the composition is at least about 1100.

5. A composition of claim 1 wherein said cryoscopic number average molecular weight of the composition is at least about 1200.

6. A composition of claim 1 wherein the composition has sufficient solubility in n-heptane at 25° C. to provide a solution containing at least 5 wt % of dissolved aluminum.

7. A composition of claim 1 wherein the composition has sufficient solubility in n-heptane at 25° C. to provide a solution containing at least 7.5 wt % of dissolved aluminum.

8. A composition of claim 1 wherein if trimethylaluminum is present in the composition, no more than about 20 mole % of the total aluminum present in the composition is in the form of trimethylaluminum, and wherein said cryoscopic number average molecular weight of the composition is at least about 1100.

9. A composition of claim 1 wherein if trimethylaluminum is present in the composition, no more than about 20 mole % of the total aluminum present in the composition is in the form of trimethylaluminum, and wherein said cryoscopic number average molecular weight of the composition is at least about 1200.

10. A composition of claim 1 wherein if trimethylaluminum is present in the composition, no more than about 20 mole % of the total aluminum present in the composition is in the form of trimethylaluminum, and wherein the composition has sufficient solubility in n-heptane at 25° C. to provide a solution containing at least 5 wt % of dissolved aluminum.

11. A composition of claim 1 wherein if trimethylaluminum is present in the composition, no more than about 20 mole % of the total aluminum present in the composition is in the form of trimethylaluminum, and wherein the composition has sufficient solubility in n-heptane at 25° C. to provide a solution containing at least 7.5 wt % of dissolved aluminum.

12. A composition of claim 1 wherein if trimethylaluminum ispresent in the composition, no more than about 10 mole % of the total aluminum present in the composition is in the form of trimethylaluminum, and wherein said cryoscopic number average molecular weight of the composition is at least about 1100.

13. A composition of claim 1 wherein if trimethylaluminum is present in the composition, no more than about 10 mole % of the total aluminum present in the composition is in the form of trimethylaluminum, and wherein said cryoscopic number average molecular weight of the composition is at least about 1200.

14. A composition of claim 1 wherein if trimethylaluminum is present in the composition, no more than about 10 mole % of the total aluminum present in the composition is in the form of trimethylaluminum, and wherein the composition has sufficient solubility in n-heptane at 25° C. to provide a solution containing at least 5 wt % of dissolved aluminum.

15. A composition of claim 1 wherein if trimethylaluminum is present in the composition, no more than about 10 mole % of the total aluminum present in the composition is in the form of trimethylaluminum, and wherein the composition has sufficient solubility in n-heptane at 25° C. to provide a solution containing at least 7.5 wt % of dissolved aluminum.

16. A composition of claim 1 wherein said cryoscopic number average molecular weight of the composition is at least about 1100, and wherein the composition has sufficient solubility in n-heptane at 25° C. to provide a solution containing at least 5 wt % of dissolved aluminum.

17. A composition of claim 1 wherein said cryoscopic number average molecular weight of the composition is at least about 1100, and wherein the composition has sufficient solubility in n-heptane at 25° C. to provide a solution containing at least 7.5 wt % of dissolved aluminum.

18. A composition of claim 1 wherein said cryoscopic number average molecular weight of the composition is at least about 1200, and wherein the composition has sufficient solubility in n-heptane at 25° C. to provide a solution containing at least 5 wt % of dissolved aluminum.

19. A composition of claim 1 wherein said cryoscopic number average molecular weight of the composition is at least about 1200, and wherein the composition has sufficient solubility in n-heptane at 25° C. to provide a solution containing at least 7.5 wt % of dissolved aluminum.

20. A composition of claim 1 wherein if trimethylaluminum is present in the composition, no more than about 20 mole % of the total aluminum present in the composition is in the form of trimethylaluminum, wherein said cryoscopic number average molecular weight of the composition is at least about 1100, and wherein the composition has sufficient solubility in n-heptane at 25° C. to provide a solution containing at least 5 wt % of dissolved aluminum.

21. A composition of claim 1 wherein if trimethylaluminum is present in the composition, no more than about 20 mole % of the total aluminum present in the composition is in the form of trimethylaluminum, wherein said cryoscopic number average molecular weight of the composition is at least about 1100, and wherein the composition has sufficient solubility in n-heptane at 25° C. to provide a solution containing at least 7.5 wt % of dissolved aluminum.

22. A composition of claim 1 wherein if trimethylaluminum is present in the composition, no more than about 20 mole % of the total aluminum present in the composition is in the form of trimethylaluminum, wherein said cryoscopic number average molecular weight of the composition is at least about 1200, and wherein the composition has sufficient solubility in n-heptane at 25° C. to provide a solution containing at least 5 wt % of dissolved aluminum.

23. A composition of claim 1 wherein if trimethylaluminum is present in the composition, no more than about 20 mole % of the total aluminum present in the composition is in the form of trimethylaluminum, wherein said cryoscopic number average molecular weight of the composition is at least about 1200, and wherein the composition has sufficient solubility in n-heptane at 25° C. to provide a solution containing at least 7.5 wt % of dissolved aluminum.

24. A composition of claim 1 wherein if trimethylaluminum is present in the composition, no more than about 10 mole % of the total aluminum present in the composition is in the form of trimethylaluminum, wherein said cryoscopic number average molecular weight of the composition is at least about 1100, and wherein the composition has sufficient solubility in n-heptane at 25° C. to provide a solution containing at least 5 wt % of dissolved aluminum.

25. A composition of claim 1 wherein if trimethylaluminum is present in the composition, no more than about 10 mole % of the total aluminum present in the composition is in the form of trimethylaluminum, wherein said cryoscopic number average molecular weight of the composition is at least about 1100, and wherein the composition has sufficient solubility in n-heptane at 25° C. to provide a solution containing at least 7.5 wt % of dissolved aluminum.

26. A composition of claim 1 wherein if trimethylaluminum is present in the composition, no more than about 10 mole % of the total aluminum present in the composition is in the form of trimethylaluminum, wherein said cryoscopic number average molecular weight of the composition is at least about 1200, and wherein the composition has sufficient solubility in n-heptane at 25° C. to provide a solution containing at least 5 wt % of dissolved aluminum.

27. A composition of claim 1 wherein if trimethylaluminum is present in the composition, no more than about 10 mole % of the total aluminum present in the composition is in the form of trimethylaluminum, wherein said cryoscopic number average molecular weight of the composition is at least about 1200, and wherein the composition has sufficient solubility in n-heptane at 25° C. to provide a solution containing at least 7.5 wt % of dissolved aluminum.

28. A composition which comprises a solution of methylaluminoxane in a non-aromatic hydrocarbon solvent, wherein:
   a) the solution is either free of aluminum in the form of trimethylaluminum or if trimethylaluminum is present in the solution, not more than about 30 mole % of the total aluminum present in the solution is in the form of trimethylaluminum;
   b) the solution has a total dissolved aluminum content of at least 5 wt %, based on the total weight of all dissolved aluminum components of the methylaluminoxane plus the weight of the non-aromatic hydrocarbon solvent;
   c) the solution contains, if any, no more than 0.75 grams of aromatic hydrocarbon per mole of dissolved aluminum in the solution; and
   d) the methylaluminoxane in said solution has a cryoscopic number average molecular weight as determined in benzene of at least about 1000 atomic mass units.

29. A composition of claim 28 wherein said total dissolved aluminum content of said solution is at least about 7.5 wt % of dissolved aluminum.

30. A composition of claim 28 wherein said cryoscopic number average molecular weight is at least about 1100 atomic mass units.

31. A composition of claim 28 wherein said total dissolved aluminum content of said solution is at least about 7.5 wt % of dissolved aluminum, and wherein said cryoscopic number average molecular weight is at least about 1200 atomic mass units.

32. A composition of claim 28 wherein the methylaluminoxane used in forming said solution is a residual product formed by subjecting a precursor solution of a methylaluminoxane in an aromatic hydrocarbon solvent to distillation at a temperature no higher than about 30° C. under reduced pressure of below $1 \times 10^{-5}$ millimeters of mercury to form a residual product which (A) is a solid at 25° C.; (B) has a total aluminum content in the range of about 39 to about 47 wt % based on the total weight of the residual product in the solid state; (C) is either free of aluminum in the form of trimethylaluminum or if trimethylaluminum is present in the residual product, not more than about 30 mole % of the total aluminum present in the residual product is in the form of trimethylaluminum; (D) in the solid state contains no more than about 2000 ppm (wt/wt) of aromatic hydrocarbon; (E) has a cryoscopic number average molecular weight as determined in benzene of at least about 1000 atomic mass units; and (F) has sufficient solubility in n-heptane at 25° C. to provide a solution containing at least 4 wt % of dissolved aluminum.

33. A composition of claim 32 wherein the methylaluminoxane of said precursor solution is formed by partial hydrolysis of trimethylaluminum.

34. A composition of claim 32 wherein the methylaluminoxane of said precursor solution is formed by treating trimethylaluminum with a compound containing an oxygen-carbon bond.

35. A composition of claim 28 wherein said non-aromatic hydrocarbon consists essentially of (a) one or more alkane, alkene, alkadiene, cycloalkane, cycloalkene, cycloalkadiene, alkye or non-aromatic polyunsaturated hydrocarbons that exist as a liquid at least throughout the range of about 20 to about 30° C.; or (b) a mixture of at least two different members of (a); or (c) at least one member of (a) and/or (b), and one or more alkane hydrocarbons that exist as a liquid at least throughout the range of about 20 to about 30° C.

36. A composition of claim 28 wherein said non-aromatic hydrocarbon consists essentially of one or more alkane or cycloalkane hydrocarbons that exist as a liquid at least throughout the range of about 20 to about 30° C., or a mixture of at least one said alkane and at least one said cycloalkane hydrocarbon.

37. A method of preparing a methylaluminoxane composition of enhanced solubility characteristics, which method comprises subjecting a solution of methylaluminoxane in an aromatic hydrocarbon solvent to distillation at a temperature no higher than about 30° C. under reduced pressure of about $1 \times 10^{-5}$ millimeters of mercury or less to form a methylaluminoxane composition in the form of a residual product which (A) is a solid at 25° C.; (B) has a total aluminum content in the range of about 39 to about 47 wt % based on the total weight of the residual product in the solid state; (C) is either free of aluminum in the form of trimethylaluminum or if trimethylaluminum is present in the residual product, not more than about 30 mole % of the total aluminum present in the residual product is in the form of trimethylaluminum; (D) contains in the solid state no more than about 2000 ppm (wt/wt) of aromatic hydrocarbon; (E) has a cryoscopic number average molecular weight as determined in benzene of at least about 1000 atomic mass units; and (F) has sufficient solubility in n-heptane at 25° C. to provide a solution containing at least 4 wt % of dissolved aluminum.

38. A method of claim 37 wherein if trimethylaluminum is present in said residual product, no more than about 20 mole % of the total aluminum present in said residual product is in the form of trimethylaluminum.

39. A method of claim 37 wherein if trimethylaluminum is present in said residual product, no more than about 10 mole % of the total aluminum present in said residual product is in the form of trimethylaluminum.

40. A method of claim 37 wherein said cryoscopic number average molecular weight of said residual product is at least about 1100.

41. A method of claim 37 wherein said cryoscopic number average molecular weight of said residual product is at least about 1200.

42. A method of claim 37 wherein said residual product has sufficient solubility in n-heptane at 25° C. to provide a solution containing at least 5 wt % of dissolved aluminum.

43. A method of claim 37 wherein said residual product has sufficient solubility in n-heptane at 25° C. to provide a solution containing at least 7.5 wt % of dissolved aluminum.

44. A method of claim 37 wherein if trimethylaluminum is present in said residual product, no more than about 20 mole % of the total aluminum present in said residual product is in the form of trimethylaluminum, wherein said cryoscopic number average molecular weight of said residual product is at least about 1100, and wherein said residual product has sufficient solubility in n-heptane at 25° C. to provide a solution containing at least 5 wt % of dissolved aluminum.

45. A method of claim 37 wherein if trimethylaluminum is present in said residual product, no more than about 20 mole % of the total aluminum present in said residual product is in the form of trimethylaluminum, wherein said cryoscopic number average molecular weight of said residual product is at least about 1100, and wherein the residual product has sufficient solubility in n-heptane at 25° C. to provide a solution containing at least 7.5 wt % of dissolved aluminum.

46. A method of claim 37 wherein if trimethylaluminum is present in said residual product, no more than about 20 mole % of the total aluminum present in said residual product is in the form of trimethylaluminum, wherein said cryoscopic number average molecular weight of said residual product is at least about 1200, and wherein said residual product has sufficient solubility in n-heptane at 25° C. to provide a solution containing at least 5 wt % of dissolved aluminum.

47. A method of claim 37 wherein if trimethylaluminum is present in said residual product, no more than about 20 mole % of the total aluminum present in said residual product is in the form of trimethylaluminum, wherein said cryoscopic number average molecular weight of said residual product is at least about 1200, and wherein said residual product has sufficient solubility in n-heptane at 25° C. to provide a solution containing at least 7.5 wt % of dissolved aluminum.

48. A method of claim 37 wherein if trimethylaluminum is present in said residual product, no more than about 10 mole % of the total aluminum present in said residual product is in the form of trimethylaluminum, wherein said cryoscopic number average molecular weight of said residual product is at least about 1100, and wherein said residual product has sufficient solubility in n-heptane at 25° C. to provide a solution containing at least 5 wt % of dissolved aluminum.

49. A method of claim 37 wherein if trimethylaluminum is present in said residual product, no more than about 10 mole % of the total aluminum present in said residual product is in the form of trimethylaluminum, wherein said cryoscopic number average molecular weight of said residual product is at least about 1100, and wherein said residual product has sufficient solubility in n-heptane at 25° C. to provide a solution containing at least 7.5 wt % of dissolved aluminum.

50. A method of claim 37 wherein if trimethylaluminum is present in said residual product, no more than about 10 mole % of the total aluminum present in said residual product is in the form of trimethylaluminum, wherein said cryoscopic number average molecular weight of said residual product is at least about 1200, and wherein said residual product has sufficient solubility in n-heptane at 25° C. to provide a solution containing at least 5 wt % of dissolved aluminum.

51. A method of claim 37 wherein if trimethylaluminum is present in said residual product, no more than about 10 mole % of the total aluminum present in said residual product is in the form of trimethylaluminum, wherein said cryoscopic number average molecular weight of said residual product is at least about 1200, and wherein said residual product has sufficient solubility in n-heptane at 25° C. to provide a solution containing at least 7.5 wt % of dissolved aluminum.

52. A method of increasing the solubility of a methylaluminoxane in a non-aromatic hydrocarbon solvent and providing a solution of such methylaluminoxane in a non-aromatic hydrocarbon, which method comprises:

I) subjecting a solution of methylaluminoxane in an aromatic hydrocarbon solvent to distillation at a temperature no higher than about 300° C. under reduced pressure of below $1 \times 10^{-5}$ millimeters of mercury to form a solid methylaluminoxane residue which (A) is a solid at 25° C.; (B) has a total aluminum content in the range of about 39 to about 47 wt % based on the total weight of the residual product in the solid state; (C) is either free of aluminum in the form of trimethylaluminum or if trimethylaluminum is present in the residual product, not more than about 30 mole % of the total aluminum present in the residual product is in the form of trimethylaluminum; (D) contains in the solid state no more than about 2000 ppm (wt/wt) of aromatic hydrocarbon; (E) has a cryoscopic number average molecular weight as determined in benzene of at least about 1000 atomic mass units; and (F) has sufficient solubility in n-heptane at 25° C. to provide a solution containing at least 4 wt % of dissolved aluminum; and II) dissolving such solid methylaluminoxane residue in a non-aromatic hydrocarbon solvent in an amount such that the resultant solution contains at least 5 wt % of dissolved aluminum based on the total weight of the foregoing specified components.

53. A method of claim 52 wherein said resultant solution contains at least 7.5 wt % of dissolved aluminum based on the total weight of said specified components.

54. A method of claim 52 wherein said cryoscopic number average molecular weight is at least about 1100 atomic mass units.

55. A method of claim 52 wherein said resultant solution contains at least 7.5 wt % of dissolved aluminum, and wherein said cryoscopic number average molecular weight is at least about 1200 atomic mass units.

56. A method of claim 52 wherein the methylaluminoxane in the solution of methylaluminoxane in an aromatic hydrocarbon solvent in I) is a methylaluminoxane formed by partial hydrolysis of trirnethylaluminum.

57. A method of claim 52 wherein the methylaluminoxane in the solution of methylaluminoxane in an aromatic hydrocarbon solvent in I) is a methylaluminoxane formed by treating trimethylaluminum with a compound containing an oxygen-carbon bond.

58. A method of claim 52 wherein said non-aromatic hydrocarbon solvent consists essentially of (a) one or more alkene, alkadiene, cycloalkane, cycloalkene, cycloalkadiene, alkyne, or non-aromatic polyunsaturated hydrocarbons that exist as a liquid at least throughout the range of about 20 to about 30° C.; or (b) a mixture of at least two different members of a); or (c) at least one member of (a) and/or (b), and one or more alkane hydrocarbons that exist as a liquid at least throughout the range of about 20 to about 30° C.

59. A method of claim 52 wherein said non-aromatic hydrocarbon solvent consists essentially of one or more alkane or cycloalkane hydrocarbons that exist as a liquid at least throughout the range of about 20 to about 30° C., or a mixture of at least one said alkane and at least one said cycloalkane hydrocarbon.

* * * * *